United States Patent [19]

Humbert et al.

[11] Patent Number: 5,534,275
[45] Date of Patent: Jul. 9, 1996

[54] FOODSTUFFS CONTAINING A CEREAL INGREDIENT AND FERRIC EDTA

[75] Inventors: Robert D. Humbert; Leila Saldanha, both of Battle Creek; John Kepplinger, Portage, all of Mich.

[73] Assignee: Kellogg Company, Battle Creek, Mich.

[21] Appl. No.: 430,110

[22] Filed: Apr. 27, 1995

Related U.S. Application Data

[63] Continuation of Ser. No. 203,143, Feb. 28, 1994, abandoned.

[51] Int. Cl.$^6$ ..................................................... A23L 1/304
[52] U.S. Cl. ........................... 426/74; 426/271; 426/620; 426/648
[58] Field of Search .............................. 426/74, 271, 620, 426/648

[56] References Cited

PUBLICATIONS

Clydesdale, et al., eds. pp. 55–63, (1984), "Iron Fortification of Foods".
Lerner, et al., Center for Food Safety and Applied Nutrition, FDA (1986), "A Review of the Current Position of the U.S. Food and Drug Administration on EDTA Compounds, Including sodium iron EDTA".
el Guindi, et al., BR. J. Nutri. 59: 205–213 (1988), "Iron absorption from fortified flat breads".
MacPhail, et al., Br. J. Nutri. 45: 215–227 (1981), "Factors Affectign the absorption of iron from FE(III)EDTA".
Candela, et al., J. Nutri. 114: 2204–11, (1984), "Iron Absorption by Humans and Swin from FE(III)–EDTA, Further Studies".
Cook, et al., Am. J. Clinical Nutrition 38: 648–659 (1983), "Iron fortification: an update".
MacPhail, et al., Am. J. Clin. Nutri. 59: 644–648 (1994), "EDTA and the absorption of iron from food".
Aruoma, Chemistry in Britain, 29(3): 210–214 (1993), "Free radicals and food".
International Nutritional Anemia Consultative Group (Sep. 1993) "Iron EDTA for Food Fortification".
Hurrell, et al, Br. J. Nutri. 71: 85–93 (1994), "NaFe$^{3+}$ as a food Fortificant: influence on zinc, calcium and copper metabolism in the rat".
Whittaker, et al., Br. J. Nutri. 63: 587–595 (1990), "Effect of EDTA on the bioavailability to rats of fortification iron used in Egyptian balady bread".
Reddy, National Institute of Nutrition, Indian Council of Medical Research (1991), "Preventing Specific Micronutrient Deficiencies".
Whittaker, et al., Regulatory Toxicology and Pharmacology 18: 419–427 (1993), "Toxicological Profile, Current Use, and Regulatory Issues on EDTA Compounds for Assessing Use of Sodium Iron EDTA for Food Fortification".

*Primary Examiner*—Helen Pratt
*Attorney, Agent, or Firm*—Felfe & Lynch

[57] ABSTRACT

The invention provides for a ready-to-eat cereal product fortified with ferric EDTA as the iron source. The cereal product comprises about 0.1 to about 300 mg of ferric EDTA product per ounce of said cereal product, preferably 13 to 140 mg per ounce. The total iron content present is in the range of about 0.1 to about 39 mg per ounce of the cereal product, and preferably about 1.8 to 18 mg per ounce. The cereal product can also be fortified with a ferric EDTA complex in combination with an additional iron fortificant. The invention also provides for a method to prevent or treat iron-deficiency anemia by administering a ferric EDTA fortified ready-to-eat cereal.

15 Claims, No Drawings

FOODSTUFFS CONTAINING A CEREAL INGREDIENT AND FERRIC EDTA

This application is a continuation, of application Ser. No. 08/203,143, filed Feb. 28, 1994, now abandoned.

FIELD OF THE INVENTION

This invention is related to the fortification of ready-to-eat cereal products with iron. The iron compound utilized in the fortification process is a chelated iron compound that provides surprising and unexpected advantages. The form of iron fortificant is one that provides a R-T-E cereal with the added combined advantages of improved bioavailability, oxidative stability, excellent vibrancy of color or brightness characteristics and little, if any, metallic offtaste.

BACKGROUND OF THE INVENTION

Approximately one-fifth of the world's population suffer from some level of nutritional iron deficiency. Young children and women of childbearing age are the most adversely affected by anemia and other iron deficiency related conditions. Anemia during pregnancy can lead to risk of premature labor, (Lieberman et al., Am.J.Obstet.Gyn. 159:107–114) and an increased perinatal morbidity and mortality, (Bothwell et al., In Iron Metabolism in Man, 1979). The development of children may also be impaired having an effect on their later performance in schools. Iron deficiency can also adversely affect laborers which results in impaired productivity, (Edgerton et al., Brit. Med.J. 2:1546–9, 1979).

Heme iron, which is derived primarily from hemoglobin and myoglobin in meat, is transferred as intact porphyrin complex to intestinal cells, where the heme oxygenase enzyme rapidly releases the iron. It blends with other iron taken up by the cell before the regulated transfer to the blood stream occurs. This form of iron is readily absorbed and is generally not affected by the contents of the meal with which the heme containing food is consumed. The nonheme iron has a heterogenous origin, being derived from vegetable foods and inorganic forms of iron, and can be used to fortify foods to increase the level of iron present in the food.

Non-heme iron, which is derived from plant foods and fortified foods is not as well absorbed as heme (meat) iron. Furthermore, beverages such as coffee and tea consumed at meal time and other components can contribute to poor absorption of non-heme iron.

The addition of ascorbic acid or vitamin C can enhance the iron absorption in the diet, generally without affecting consumer acceptability. However, ascorbic acid is expensive compared to iron fortification and when exposed to oxygen and moisture can be unstable under storage conditions. In cases where food preparation involves baking, prolonged boiling or reheating, ascorbic acid is incompatible with iron fortification.

The most efficient and cost-effective way of preventing and treating iron deficiency is to fortify food products with a form of iron that provides for adequate absorption.

Recently, a sodium ferric ethylenediaminetetraacetic acid complex (hereinafter "ferric EDTA") has been studied primarily for fortification purposes due to its chemical stability, (See Fe Iron EDTA for Food Fortification—A report of the International Nutritional Anemia Consultative Group). It has been found to be suitable for fortifying foods that require prolonged storage or high temperatures during preparation.

Ferric EDTA is a pale-yellow water-soluble powder that can be added to many food vehicles. In addition, when ferric EDTA is consumed with foods containing large quantities of absorption inhibitors, iron is protected from agents which inhibit its absorption. Ferric EDTA has been reported to be two to three times more bioavailable than iron presented as a $FeSO_4$ complex in some diets. Furthermore, ferric EDTA is more stable under adverse storage conditions and is unaffected by cooking.

Other known uses of ferric EDTA, under experimental conditions, are found in food ingredients or condiments, i.e., fish sauce in Thailand (Garby et al., 1974, Ann.Tro.Med.Parasitol. 68: 467–76), curry powder in South Africa (Macphail et al. Experimental Fortificants, in: Clydesdale FM et al. eds. Iron Fortification of Foods, 1985), Egyptian flat bread (Guindi et al., Brit.J. Nutr. 59:205–213, 1988), sugar in Guatemala (MacPhail et al., Br. J. Nutr. 45: 215–227, 1981). Absorption of iron in dietary foods such as flat breads has also been studied in Guindi et al., 1988.

This is the first known use of ferric EDTA fortification in a ready-to-eat cereal. The R-T-E cereal product is often added to a liquid, e.g., milk, and then consumed without reheating or cooking. The R-T-E cereal product is prepared with ferric EDTA by either incorporating it into the cereal mix prior to cooking or by spraying a ferric EDTA solution onto the finished cereal product.

It has been found that ferric EDTA provides for the best combined results for iron fortification, in terms of bioavailability, brightness characteristics, metallic offtaste and oxidative stability after exposure to hot room tests. It was found that ferric EDTA fortification results in improved bioavailability, excellent brightness tests, little metallic offtaste and excellent oxidative stability.

These unexpected properties for the ferric EDTA fortified R-T-E cereal product described above have not been established prior to this application. Surprisingly, the addition of ferric EDTA does not alter the intensity of the brightness or flavor of the finished cereal product.

Thus, it is a principal object of this invention to provide for a ready-to-eat cereal which is fortified with a ferric EDTA complex. The use of ferric EDTA as an iron fortificant in a R-T-E cereal produces a product which is organoleptically acceptable to consumers. The color, odor, and taste of the product is not adversely affected by the addition of the ferric EDTA fortificant and the bioavailability of the iron in the R-T-E cereal product appeared not be affected by the constituents of cereals which might inhibit the absorption of other forms of iron.

It is a further object of the invention to provide for fortifying a ready-to-eat cereal with ferric EDTA in combination with an additional source of iron, i.e., reduced iron, ferrous sulfate.

It is a further object of the invention to provide a method to prevent or to treat iron-deficiency anemia by administering the ready-to-eat cereal of the invention to individuals or population groups in need of such treatment.

SUMMARY OF THE INVENTION

This invention provides for a ready-to-eat cereal (R-T-E) product which is fortified with a compound of iron complexed with EDTA. Fortifying a R-T-E cereal with this particular iron complex yields surprising results in a novel cereal product which is unaffected by the ferric complex in the organoleptic qualities, i.e., its color, odor, stability and taste. The ferric EDTA is present in the R-T-E cereal product in the range 0.1 mg to 300 mg per ounce, or preferably 13 mg to 140 mg per ounce. The total iron content in the R-T-E cereal ranges from 0.1 to 30 mg per ounce of cereal product, or preferably 1.8 to 18 mg/ounce of cereal product.

The invention further provides for the use of ferric EDTA in combination with an additional iron fortificant i.e., reduced iron, ferrous fumarate, ferrous sulfate, or ferric citrate.

The invention also provides for a method of preventing or treating iron-deficiency anemia by administration of the fortified R-T-E cereal of the invention to those in need of such treatment.

DETAILED DESCRIPTION OF THE INVENTION

Examples of R-T-E cereal products fortified with ferric EDTA are set forth below. This invention will be better understood by reference to the following examples, which are included here for purposes of exemplification and are not to be construed as limitations.

EXAMPLE 1

A ready-to-eat cereal product fortified with ferric EDTA can be prepared by using the following ingredients:

TABLE 1

| Ingredient | % Dry Basis | Weight (lbs) |
| --- | --- | --- |
| Corn Flaking Grits | 87.326 | 350.000 |
| Concentrated Flavor | 12.428 | 72.500 |
| Ferric EDTA[1] | 0.226 | 1.141 |
| Vitamins | 0.020 | 0.069 |

[1]The iron content of a typical ferric EDTA can vary but the compound used in this example is approximately 13%.

The R-T-E cereal product is prepared as follows: A cooker is preheated for 30 minutes at 20 psi steam (259° F.). The corn flaking grits, concentrated flavor, vitamins and ferric EDTA are placed in the cooker and 20 psi steam is applied for about 100 minutes, preferably about 105 minutes. The cooked cereal is then cooled to room temperature and separated. The cereal is dried to a moisture of 12%, flaked and then dried to a final moisture of 3%. Vitamins are sprayed on after drying. The iron content of the finished R-T-E cereal product is 11.46 mg/ounce.

The ferric EDTA content of the finished product ranges from 0.1 to 300 mg per one ounce (28.4 g) serving, or preferably 13 mg to 140 mg per ounce. The iron fortification range of approximately 0.1 to 39 mg/oz., or preferably 1.8 to 18 mg/oz.

EXAMPLE 2

The ready-to-eat cereal can also be prepared without adding the iron fortificant to the cereal dough. Ferric EDTA can be sprayed onto the product after the cereal pieces are formed.

TABLE 2

| Ingredients | % As Is | Weight (gms) |
| --- | --- | --- |
| Water | 81.1 | 811.000 |
| Ferric EDTA | 18.9 | 189.000 |

A solution is prepared by dissolving ferric EDTA in water in the above proportions.

The R-T-E cereal product is produced as described in Example 1, without the ferric EDTA. After the cereal pieces of approximately 3% moisture level are produced, a ferric EDTA/water solution is sprayed on the finished product at a rate of 5.00 gm per pound of product. The ferric EDTA content of the finished product ranges from 0.1 to 300 mg per one ounce (28.4 g) serving, or preferably 13 mg to 140 mg per ounce. The iron fortification range of approximately 0.1 to 39 mg/oz., preferably 1.8 to 18 mg/oz or about 7 mg per ounce.

The feasibility of using other iron sources was also tested. The ferric EDTA component of the R-T-E cereal of example 1 was replaced with reduced iron, ferrous fumarate, and ferrous sulfate, and the samples were tested for three characteristics: 1) color or brightness; 2) metallic offtaste; and 3) oxidative stability. The individual tests are discussed in further detail below.

EXAMPLE 3

As previously mentioned, ferric EDTA is a pale yellow powder that is soluble in water and has a high stability constant. As the iron content of the cereal is increased, the duller the appearance of the cereal. A dull finished product can also be unattractive to consumers. Thus, combining the iron source with food ingredients to prepare a processed product can often adversely affect the food product and can result in unwanted discoloration or dullness of the finished product. Thus, R-T-E cereal products with various sources of iron fortification were tested for its effect on the intensity of the brightness or the vibrancy of color in the finished product.

Samples were produced according to the example 1, substituting ferric EDTA with reduced iron, ferrous fumarate and ferrous sulfate. The iron contents for these samples were 11.4 mg, 11.7 mg and 6.3 mg per ounce respectively. These samples were used for comparative stability and sensory analysis.

The samples were evaluated by 17 professionally trained panelists. The appearance of the cereal was evaluated. Vibrancy of the color or the intensity of the brightness of the cereal was defined on a 0–10 point scale. The illumination was white.

The four products fortified with iron in different forms were compared and the results are set forth below:

TABLE 3

| Iron Source | Brightness Value* |
| --- | --- |
| Reduced Iron | 5.1 A |
| Ferric EDTA | 5.4 A |
| Ferrous Fumarate | 4.1 B |
| Ferrous Sulfate | 2.7 C |

*Any brightness values having the same letter designation are not statistically significant, wherein the p value is <0.2.

The scale of from 0 to 10 points represents a measurement of the intensity of the brightness or vibrancy of the color of the flakes from no brightness to extremely bright. The ferric EDTA fortified product provided a statistically significant higher level of brightness as compared to the ferrous fumarate and ferrous sulfate samples tested.

EXAMPLE 4

The fortification of food products with metallic ions can result in an unacceptable metallic offtaste. However, it was found that use of ferric EDTA surprisingly did not significantly alter the taste of the cereal product. The data from the study is set forth below.

The cereal products were fortified with iron in the various forms and the panelists were asked to evaluate the level of metallic offtaste detectable in the cereal products.

TABLE 4

| Iron Source | Metallic Flavor* |
|---|---|
| Reduced Iron | 1.3 A |
| Ferric EDTA | 2.3 A |
| Ferrous Fumarate | 4.1 B |
| Ferrous Sulfate | 4.7 B |

*Any brightness values having the same letter designation are not statistically significant, wherein the p value is <0.2.

The scale of from 0 to 10 points represents the measurement of the intensity of metallic flavor from no metallic taste to high metallic flavor. The ferric EDTA fortified product provided a statistically significant lower level of metallic offtaste as compared to the ferrous fumarate and ferrous sulfate samples tested.

EXAMPLE 5

In order to test the stability of the iron fortified cereals, the R-T-E cereal samples prepared using four different sources of iron were placed in a hot room and exposed to a temperature of 100° F. over a four week period. Measurements were taken at two and four week intervals.

TABLE 5

| Iron Source | Hexanal* Value | Rancid Odor Value | Off Odor Value |
|---|---|---|---|
| Reduced Iron | 0.76 ± 8.52 | 1.22 ± 0.70 | 1.17 ± 0.50 |
| Ferric EDTA | 0.40 ± 0.22 | 0.56 ± 0.43 | 0.78 ± 0.44 |
| Ferrous Fumarate | 2.37 ± 1.00 | 2.89 ± 0.62 | 2.67 ± 0.41 |
| Ferrous Sulfate | 2.13 ± 2.02 | 1.22 ± 0.57 | 2.33 ± 0.48 |

*95% confidence interval

Based on the above test results, the ferric EDTA fortified product provided a statistically significant lower level of rancid odor, off odor and hexanal value, which indicates the level of rancidity, as compared to the ferrous fumarate and ferrous sulfate samples tested.

In continuing stability tests, the ferric EDTA is expected to improve in stability in comparison to the other ferric samples tested.

EXAMPLE 6

This example establishes a greater relative iron biological availability with ferric EDTA fortification. The relative iron availability of various iron compounds in a ready-to-eat breakfast cereal was tested using a widely accepted method, commonly referred to as the rat hemoglobin regeneration method, (modified AOAC method for assessment of relative iron bioavailability), see Williams, S. ed. Official methods of analysis of the Association of Official Analytical Chemists, 14th ed. Arlington, Va. AOAC, 1984; Fritz, J. C. et al., Collaborative Study of rat hemoglobin repletion test for bioavailability of iron, AOAC 1974, 57: 513–517. The testing for relative bioavailability of the various iron compounds was carried out in a series of separate experiments. In each of these experiments, ferrous sulfate was used as the standard or control compound.

Sprague Dawley rats, individually housed in temperature and light controlled units, were fed an iron deficient diet obtained from Harland Tekland Laboratories for 24 days. After this iron depletion phase, the rats were weighed and blood was drawn to test for baseline hemoglobin concentrations. These anemic animals, with hemoglobin levels between 2.9 to 4.1 g/l, were then randomly assigned to the control and test groups. Ferrous sulfate and the iron compounds in the cereal were added at concentrations of 6 and 18 and 24 mg iron/kg to the control and test diets. These diets were then fed to groups of ten animals, ad libitum, for 14 days. Iron levels in the diets, were verified by atomic absorption spectrometry (Bolin et al., J.Assoc.Off.Anal.Chem. 1977, 60:1170–1174). After the 14 day test period, hemoglobin concentrations were determined for all animals.

The bioavailability of each iron source tested relative to ferrous sulfate, was calculated by comparing gain in hemoglobin with the iron concentration in the diet by the slope ratio procedure (Finney, D. J., Statistical methods in biological assay. 2nd ed. 1964; Amine et L., Biological assessment of available iron in food products, J.Agric. Food Chem. 1974, 22:470–476.). Intercept and slope estimates were obtained for the blanks and each test diet using the ordinary least squares method. All test diet intercepts were compared to the blank diets to validate the fitting of a common intercept. Comparison of the slopes of the test diets with the standard (ferrous sulfate) was performed after fitting the data through a common intercept. Bioavailability was defined as the ratio of the slope of each diet to the slope of ferrous sulfate. The statistical program SAS V.608 was used. The slope values and ratios are set forth in Table 6.

TABLE 6

| Iron Source | Slope Value | Slope Ratio |
|---|---|---|
| Ferrous Sulfate | 0.33 ± 0.02* | 1.00 |
| Ferric EDTA | 0.31 ± 0.03* | 0.94 |
| Reduced Iron | 0.16 ± 0.03* | 0.48 |

*95% confidence interval

The slope of the line generated from ferric EDTA is similar to that from the ferrous sulfate standard. The slope value for the reduced iron sample was markedly less than the value for ferric EDTA. This indicates that the iron from ferric EDTA is absorbed at a rate not significantly different from ferrous sulphate and significantly better than reduced iron. This example establishes that ferric EDTA is superior in bioavailability to reduced iron which is commonly used for iron fortification in breakfast cereals.

EXAMPLE 7

Ferric EDTA can also be combined with additional iron sources, i.e., reduced iron, to fortify ready-to-eat cereal.

The following ingredients are prepared:

TABLE 7

| Ingredient | % Dry Basis | Weight (lbs) |
|---|---|---|
| Corn Flaking Grits | 87.356 | 199.9 |
| Concentrated Flavor | 12.428 | 41.5 |
| Ferric EDTA | 0.149 | 0.294 |
| Reduced Iron | 0.013 | 0.026 |
| Vitamins | 0.020 | 0.040 |
| Sucrose | 0.034 | 0.068 |

The R-T-E cereal product is prepared as follows: A cooker is preheated for 30 minutes at 20 psi steam. The above ingredients were mixed according to the parameters of example 1, and further cooked for a total cook time of about 65 minutes. The cooked cereal is then cooled to room temperature and separated. The separated cereal is allowed to temper for two and a half hours at 200° F., separated and flaked through a mill. The cereal flakes are then toasted in jet-zone oven at 450° F. The final iron content of this product is approximately 9.1 mg per ounce.

EXAMPLE 8

Ferric EDTA can also be combined with an additional iron source, i.e., reduced iron, in different types of cereal ingredients. The following ingredients are prepared:

TABLE 8

| Ingredient | % Dry Basis | Weight (lbs) |
| --- | --- | --- |
| Rice | 87.120 | 199.4 |
| Concentrated Flavor | 12.686 | 42.3 |
| Ferric EDTA | 0.188 | 0.376 |
| Reduced Iron | 0.006 | 0.013 |

The R-T-E cereal product is prepared as follows: A cooker is preheated for 30 minutes at 20 psi steam. The rice was steamed with the iron at low gear without water for 20 minutes at 17 psi (254° F.). The flavoring is added and cooked for 15 minutes in high gear. The total cook time was one hour and 20 minutes. The cooked cereal is then cooled and separated. The cereal is then dried to a moisture of 20–22%, at 180° F. for about 5 minutes. The cooked cereal is allowed to temper for two hours at;140° to 160° F. The product is gently milled to a density of 0.54 to 0.56 gm/cm³. The milled cereal pieces are then dried to 10% moisture for 10 to 20 minutes at 200° F. and tempered overnight. The cereal pieces are then toasted in a jetzone oven at 450° F. The iron content of the final product is 7.2 mg/ounce.

Based on the above results, it is clear that ferric EDTA is the best fortificant to provide the combined advantages of good oxidative stability, little metallic offtaste, bright appearance and good bioavailability for fortifying a R-T-E cereal. The foregoing examples show that the use of ferric EDTA in a R-T-E cereal product results in a more vibrant and bright appearance. Often the addition of an iron fortificant adversely affects the cereal product and results in a dull appearance which is unacceptable to the consumer.

The ferric EDTA product was also found to be the most stable of the products tested with the lowest hexanal, rancid odor and off odor values. Moreover, the ferric EDTA product was also found to be among the better tasting products, where the panelists detected little metallic offtaste.

Ferric EDTA fortification has not been used in connection with a ready-to-eat cereal prior to this preparation. Ready-to-eat cereal is unusual in that during its preparation the iron fortificant is added to either to the cereal dough product, which is cooked/heated to form the cereal piece or is sprayed onto the formed cereal piece. The cereal piece is then dried and stored for a potentially long period of time. The cereal product is not generally subjected to any further cooking means prior to consumption. In fact, often the ready-to-eat cereal is mixed with milk or other liquid, which can destabilize the cereal piece containing the iron fortificant including ferric EDTA. Many food products that are fortified with iron are required to be heated and consumed soon thereafter. The stability of the iron fortificant in a ready-to-eat product is extremely important to the palatability and physical acceptability of the product to the consumer. Any destabilization can adversely affect the overall characteristics of the product.

The use of ferric EDTA as the particular iron fortificant provides the best combined advantages of increased bioavailability, high intensity on the brightness scale, little metallic offtaste, and improved oxidative stability.

Further the combination of ferric EDTA with an additional iron fortificant such as ferrous fumarate, ferrous sulfate, reduced iron, ferric citrate, ferrous citrate, ferrous lactate, ferrous succinate, ferric phosphate, ferrous gluconate, ferrous pyrophosphate, ferrous glutamate, ferric tartrate, ferrous carbonate, ferric chloride, ferric ammonium citrate, ferrous ascorbate, ferrous glycinate, ferrous malate, and ferrous cholinisocitrate and other similar ferric or ferrous compounds which would be readily determinable by those skilled in the art, are well suited as an additional iron fortificant in ready-to-eat cereal.

Certainly other products, such as waffles, snack bars, toaster pastries, pastry products, can be fortified in the same manner with ferric EDTA, either alone or in combination with an additional iron source.

Other cereal ingredients selected from the group consisting of wheat, rice, oat, corn, barley, rye, millet, sorghum, amaranth seed and mixtures of the above can also be used in the preparation of the R-T-E cereal or other food products.

The R-T-E cereal product of this invention may also be administered to individuals or population groups to prevent or treat iron-deficiency anemia, i.e., low hemoglobin value, hematocrit value or low red blood cell count.

Furthermore, it is believed that other ingredients, which may add to the flavor or nutritional aspects of the final product, may be added to the ready-to-eat cereal product without departing from the spirit and scope of the invention. It is not intended that the present invention be limited to only the described embodiments. Modification of these embodiments will be recognized by those skilled in the art. Rather, the invention should be circumscribed by the scope of the appended claims.

What is claimed is:

1. A cooked, cereal ingredient containing, storage stable, iron fortified product, comprising:

(i) at least one cereal ingredient, (ii) a ferric EDTA compound, and (iii) no more than 12% moisture, wherein said product has bright appearance, good bioavailability of iron and little metallic offtaste.

2. The product of claim 1, wherein said product is a ready-to-eat cereal.

3. The product of claim 1, wherein said product is a snack bar.

4. The product of claim 1, wherein said product is a toaster pastry.

5. The product of claim 1, wherein said ferric EDTA compound is NaFeEDTA.

6. The product of claim 1, comprising no more than about 3% moisture.

7. The product of claim 1, comprising about 0.1 to about 300 mg of ferric EDTA per ounce of said cereal product.

8. The product of claim 1, wherein iron is present in the range of about 0.1 to 39 mg per ounce of said cereal product.

9. The product of claim 8, wherein iron is present in the range of about 1.8 to 18 mg per ounce of said cereal product.

10. The product of claim 1, wherein said cereal ingredient is selected from the group consisting of wheat, rice, oat, corn, barley, rye, millet, and amaranth.

11. The product of claim 1, further comprising at least one iron fortificant selected from the group consisting of ferrous fumarate, ferrous sulfate, reduced iron, ferric citrate, ferrous citrate, ferrous lactate, ferrous succinate, ferric phosphate, ferrous gluconate, ferrous pyrophosphate, ferrous glutamate, ferric tartrate, ferrous carbonate, ferric chloride, ferric ammonium citrate, ferrous ascorbate, ferrous glycinate, ferrous malate, and ferrous cholinisocitrate.

12. Method for preventing iron-deficiency anemia in a subject comprising administering to said subject an amount of the product of claim 11, sufficient to prevent said anemia in said subject.

13. Method to treat iron-deficiency anemia in a subject comprising administering to said subject an amount of the product of claim 11 sufficient to treat anemia in said subject.

14. Method for preventing iron-deficiency anemia in a subject comprising administering to said subject an amount of the product of claim 1, sufficient to prevent said anemia in said subject.

15. Method to treat iron-deficiency anemia in a subject comprising administering to said subject an amount of the product of claim 1 sufficient to treat said anemia in said subject.

* * * * *